United States Patent
Wright (10) Patent No.: US 9,579,687 B2
(45) Date of Patent: Feb. 28, 2017

(54) MULTISTAGE SYRINGE ASSEMBLY

(71) Applicant: Diba Industries, Inc., Danbury, CT (US)

(72) Inventor: Paul J. Wright, Cambridge (GB)

(73) Assignee: Diba Industries, Inc., Danbury, CT (US)

( * ) Notice: Subject to any disclaimer, the term of this patent is extended or adjusted under 35 U.S.C. 154(b) by 0 days.

(21) Appl. No.: 14/752,112

(22) Filed: Jun. 26, 2015

(65) Prior Publication Data

US 2015/0375256 A1    Dec. 31, 2015

Related U.S. Application Data

(60) Provisional application No. 62/018,097, filed on Jun. 27, 2014.

(51) Int. Cl.
| | |
|---|---|
| *B67D 7/60* | (2010.01) |
| *G01F 11/00* | (2006.01) |
| *B05C 17/005* | (2006.01) |
| *A61M 5/31* | (2006.01) |
| *A61M 5/19* | (2006.01) |
| *A61M 5/315* | (2006.01) |

(52) U.S. Cl.
CPC ......... *B05C 17/00593* (2013.01); *A61M 5/19* (2013.01); *A61M 5/3129* (2013.01); *A61M 5/31513* (2013.01); *A61M 2005/3131* (2013.01)

(58) Field of Classification Search
CPC .. B05C 17/00593; A61M 5/19; A61M 5/3129
USPC ............................ 222/386; 604/38, 534, 232
See application file for complete search history.

(56) References Cited

U.S. PATENT DOCUMENTS

| | | | | |
|---|---|---|---|---|
| 3,659,749 | A * | 5/1972 | Schwartz .......... | A61M 5/31596 222/129 |
| 3,885,710 | A * | 5/1975 | Cohen .................... | A61C 5/062 206/221 |
| 3,941,131 | A * | 3/1976 | Ogle ....................... | A61M 3/00 604/203 |
| 2009/0314803 | A1* | 12/2009 | Keller ................ | B01F 11/0082 222/136 |
| 2014/0276450 | A1* | 9/2014 | Bendix ............. | A61M 5/31551 604/207 |

* cited by examiner

*Primary Examiner* — Patrick M Buechner
*Assistant Examiner* — Jeremy W Carroll
(74) *Attorney, Agent, or Firm* — Dinsmore & Shohl LLP (57) ABSTRACT

A multistage syringe includes a first barrel, a second barrel, a second barrel seal assembly, and a plunger assembly. The first barrel includes a first barrel channel and the second barrel includes a second barrel channel. The first barrel couples to the second barrel such that the first barrel channel aligns with the second barrel channel along a central axis. The plunger assembly includes a plunger coupled to a plunger handle. The plunger slidably couples with the first barrel channel along the central axis and the second barrel seal assembly slidably couples with the second barrel channel along the central axis. The plunger and the second barrel seal assembly cooperate to maintain a seal as the plunger transitions between a distal end of the multistage syringe and a proximal end of the multistage syringe.

20 Claims, 9 Drawing Sheets

MULTISTAGE SYRINGE ASSEMBLY

CROSS REFERENCE TO RELATED APPLICATIONS

The present application hereby claims the benefit of Provisional U.S. Application No. 62/018,097 filed Jun. 27, 2014, entitled "Multistage Syringe Assembly."

TECHNICAL FIELD

The present specification generally relates to syringes for dispensing or aspirating fluid and, more specifically, a multi-barrel syringe for dispensing or aspirating fluid in different stages of fluid volume.

BACKGROUND

Conventional syringes only allow for a single volume of fluid to be dispensed or aspirated for a linear travel distance of the plunger. If different volumes are required, multiple, independent syringes are needed. Accordingly, a need exists for alternative syringes which dispense or aspirate fluid in different stages of fluid volume for a linear travel distance of a plunger

SUMMARY

In one embodiment, a multistage syringe includes a first barrel, a second barrel, a second barrel seal assembly, and a plunger assembly. The first barrel includes a first barrel channel and the second barrel includes a second barrel channel. The first barrel couples to the second barrel such that the first barrel channel aligns with the second barrel channel along a central axis. The plunger assembly includes a plunger coupled to a plunger handle. The plunger slidably couples with the first barrel channel along the central axis and the second barrel seal assembly slidably couples with the second barrel channel along the central axis. The plunger and the second barrel seal assembly cooperate to maintain a seal as the plunger transitions between a distal end of the multistage syringe and a proximal end of the multistage syringe.

In another embodiment, a syringe kit includes a second barrel, a second barrel seal assembly, and a plunger assembly. The second barrel includes a second barrel channel and the second barrel seal assembly slidably couples with the second barrel channel along a central axis. The plunger assembly comprises a plunger coupled to a plunger handle. The second barrel is configured couple with a syringe comprising a syringe barrel and a syringe barrel channel such that the syringe barrel channel aligns with the second barrel channel along the central axis. The plunger slidably couples with the syringe barrel channel along the central axis and the plunger and the second barrel seal assembly cooperate to maintain a seal as the plunger transitions between a distal end and a proximal end of the combination of the syringe and the syringe kit.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

In one embodiment, a multistage syringe is shown and described that enables a user to deliver different volumes of fluid at different stages with a single syringe. The multistage syringe has a primary barrel axially aligned with a secondary barrel. The secondary barrel may include a different internal diameter channel than that of the primary barrel. The multistage syringe may also include a second barrel seal assembly to aid in the transition of the plunger between the two internal diameters channels of the primary and secondary barrel. The plunger and the second barrel seal assembly cooperate to maintain a seal between the plunger and the channels of the two barrels. The second barrel seal assembly may be removably coupled to the plunger within the secondary barrel. In one embodiment, the multistage syringe delivers different volumes of fluid at near identical liner travel distances of the plunger assembly. In one embodiment, the multistage syringe changes a speed at which a fluid is delivered or aspirated for a constant linear travel speed of the plunger assembly.

Figure 1:
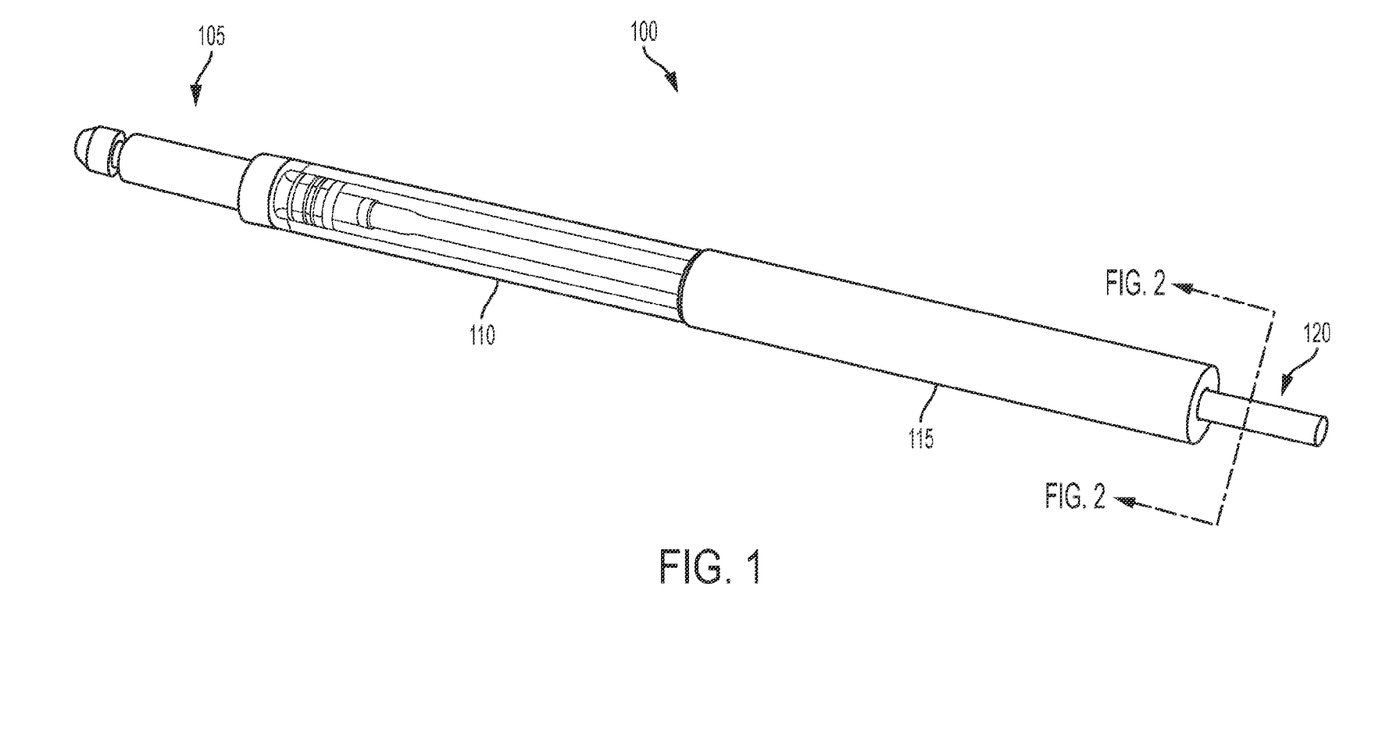
FIG. 1 is a perspective view of a multistage syringe according to one or more embodiments shown and described herein.

Referring now to FIG. 1, a multistage syringe 100 includes a first barrel 110, a second barrel 115, and a plunger assembly 120. The multistage syringe 100 retains a fluid such as a liquid or gas and either dispenses the fluid out of the multistage syringe 100 or draws (aspirate) the fluid into the multistage syringe 100. The multistage syringe 100 may be used as a medical syringe, as a liquid dispensing tool, as a tool to remove or draw fluid away from a space, or to place a fluid in a space. The space may include an enclosed volume such as, for example, a vein or artery, between two parts to be joined, etc. The multistage syringe 100 may also include a dispensing tip 105.

Referring now to FIGS. 2, 3A, 3B, and 3C, the first barrel 110 may be coupled with the second barrel 115 through an interference fit between an outer receiver radius 405 (FIG. 4B) of the first barrel 110 and an inner receiver radius 520 (FIG. 5B) of the second barrel 115 such that the first barrel channel 400 and the second barrel channel 530 are axially aligned along the central axis 200. To accomplish the coupling, the second barrel 115 may include a receiver portion 510 (FIG. 5A) in which the inner receiver radius 520 is about equal to the outer receiver radius 405 of the first barrel 110. The receiver portion 510 may include a stop 525 (FIGS. 5A and 5B). The stop 525 is a sharp transition from the inner receiver radius 520 to an inner second barrel radius 515. The first barrel 110 may include a second stop 410. The second stop 410 is a sharp transition from the outer receiver radius 405 to an outer first barrel radius. When the second barrel 115 matedly couples with the first barrel 110, a first barrel lip 420 may be situated near the stop 525. Likewise, when the second barrel 115 matedly couples with the first barrel 110, a second barrel lip 535 may make contact with the second stop 410 or may be situated near the second stop 410. All radiuses are taken from the central axis 200.

A collar space 235 is positioned between the outer receiver radius 405 of the first barrel 110, the inner receiver radius 520 of the second barrel 115, the second stop 410 of the first barrel 110, and the stop 525 of the second barrel 115. The collar space 235 may have an adhesive disposed within it to secure the first barrel 110 to the second barrel 115. In one embodiment, the collar space 235 may have a barrel gasket 240 disposed within it. The barrel gasket 240 may provide a seal between the first barrel 110 and the second barrel 115. In one embodiment, the collar space 235 may include both a barrel gasket 240 and an adhesive.

Figure 2:
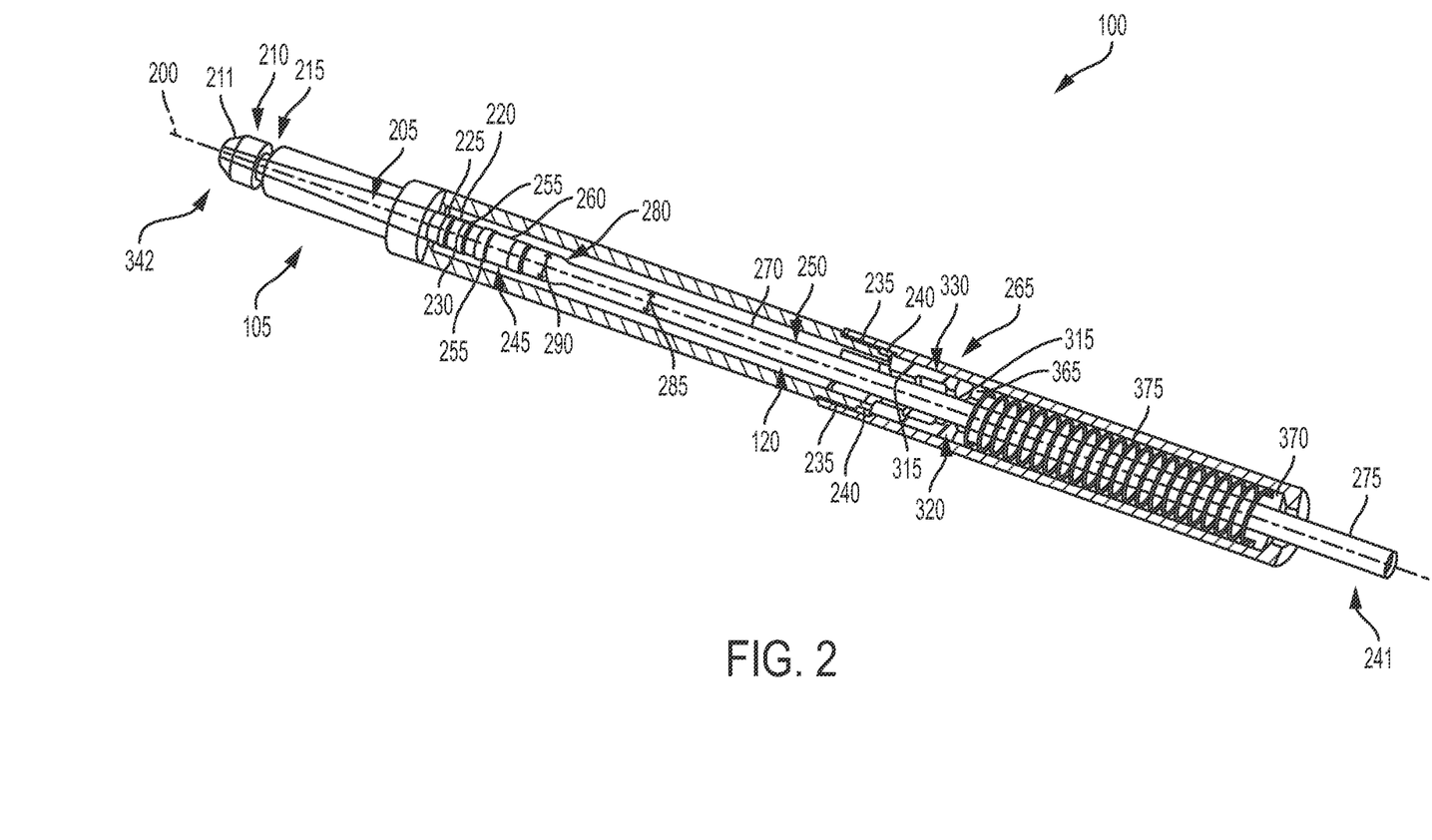
FIG. 2 is a cross-sectional view of the multistage syringe according to one or more embodiments shown and described herein.

Still referring to FIGS. 2, 3A, 3B, and 3C, the plunger assembly 120 may include a plunger handle 275 and a plunger 250. The plunger 250 may include a neck portion 270, a plunger plug 245, a taper seal 280, a shuttle engagement ring 295, and a plunger tip 283. In one embodiment, the neck portion 270, the plunger handle 275, and the taper seal 280 may be circular in shape. Referring specifically to FIG. 2, the taper seal 280 transitions a necked diameter 285 to a tapered diameter 290. In one embodiment, the tapered diameter 290 may have about the same outer diameter as the plunger plug 245 which may be about equal to an inner first barrel radius 430 (FIG. 4). The necked diameter 285 may be sized to slidably couple with a first gasket 320 and a retainer lip 316 of the shuttle 330 while maintaining a seal between the neck portion 270, the first gasket 320, and the shuttle 330. In one embodiment, the outer diameter of the tapered diameter 290 and the plunger plug 245 may be about equal to the inner first barrel radius 430.

Figure 3A:
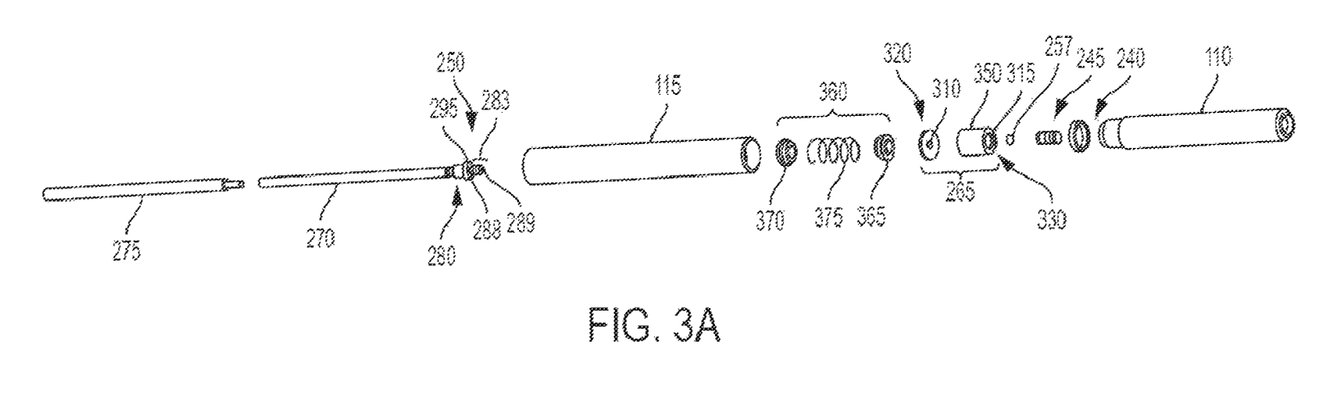
FIG. 3A is an exploded right, front perspective view of the multistage syringe according to one or more embodiments shown and described herein.
Figure 3B:
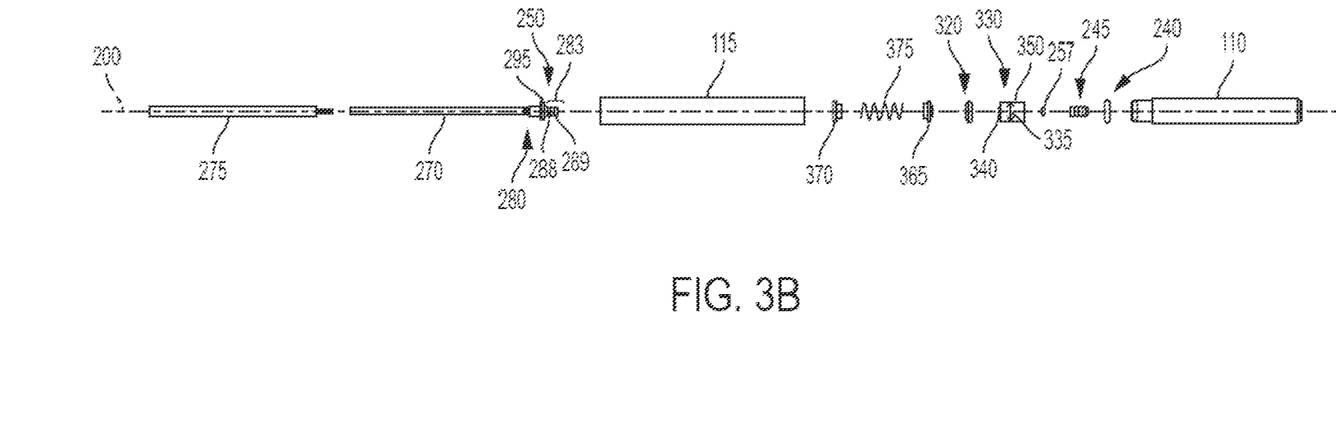
FIG. 3B is an exploded top view of the multistage syringe according to one or more embodiments shown and described herein.
Figure 3C:
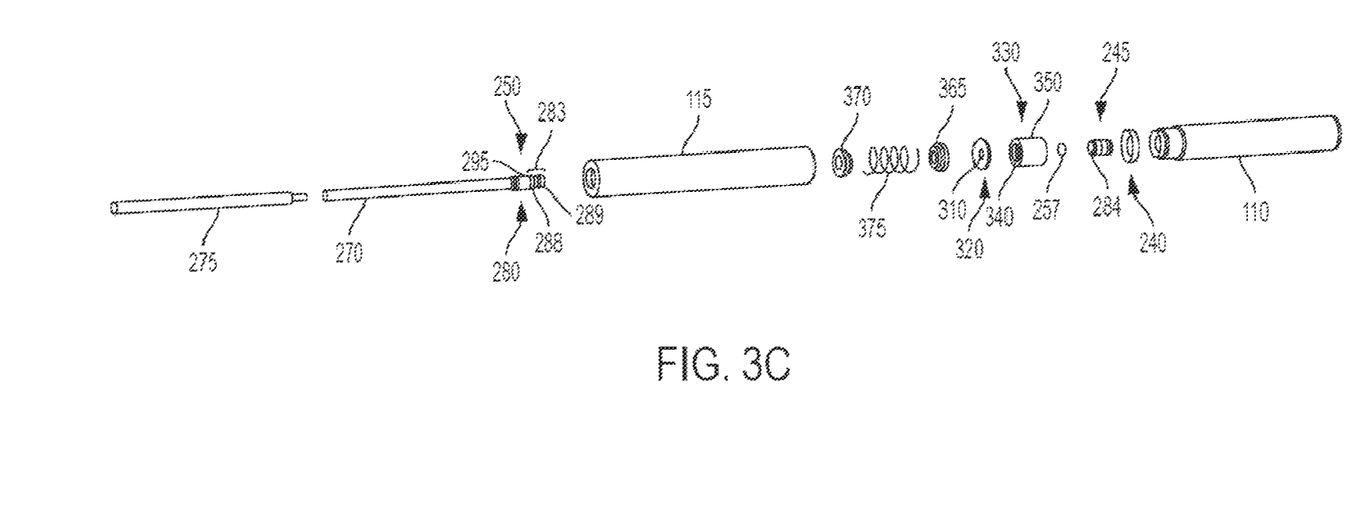
FIG. 3C is an exploded right, rear perspective view of the multistage syringe according to one or more embodiments shown and described herein.
Figure 4A:
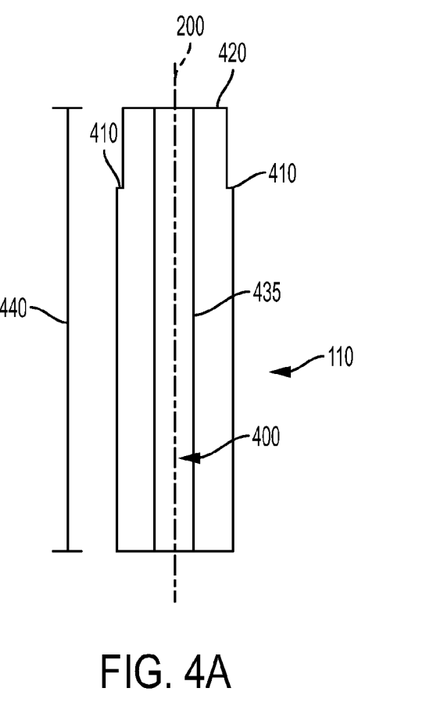
FIG. 4A is a lengthwise cross-sectional view of a first barrel according to one or more embodiments shown and described herein.
Figure 9:
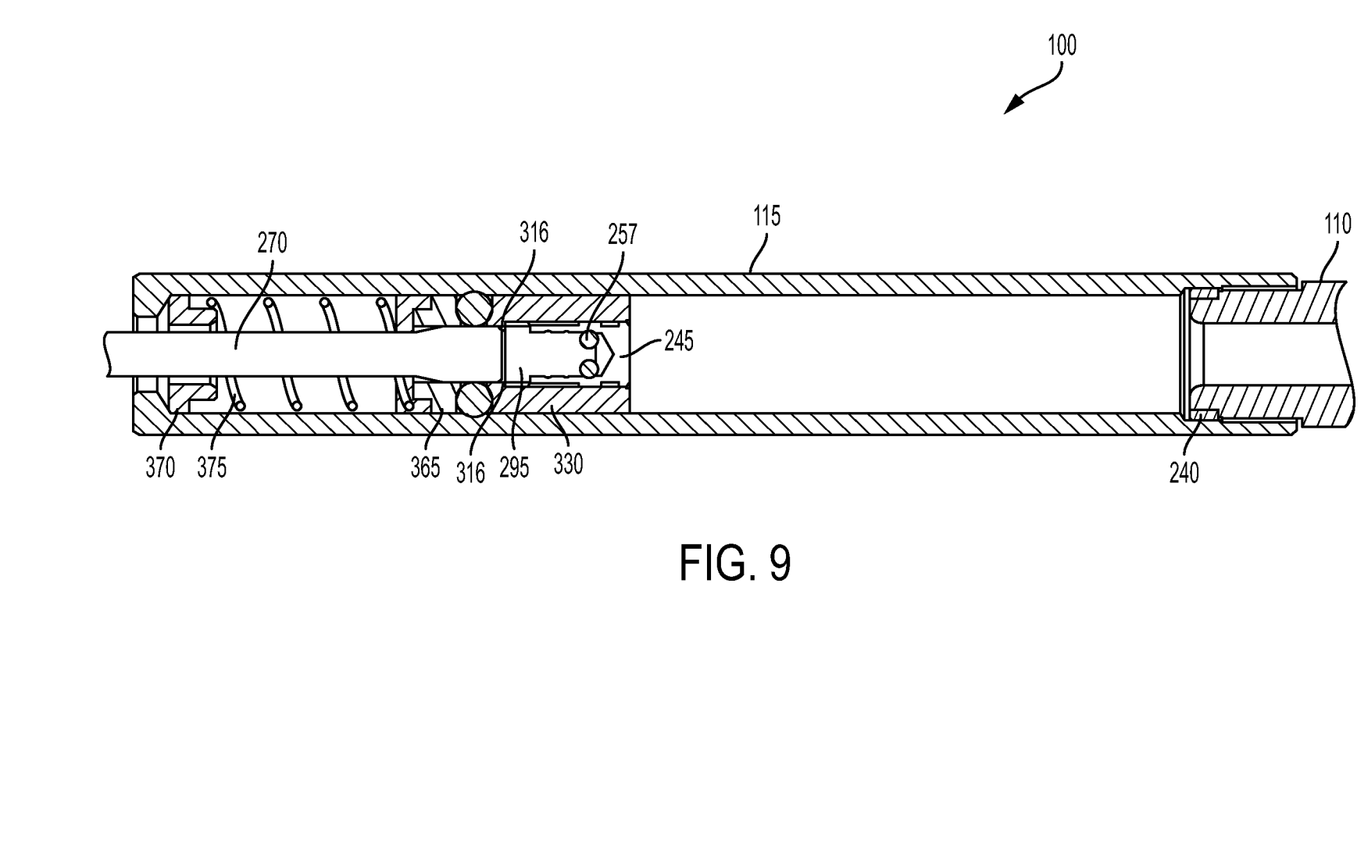
FIG. 9 is cross-sectional top view of a shuttle of the multistage syringe in the aspirated position according to one or more embodiments shown and described herein.

The plunger tip 283 at the distal end 342 of the plunger assembly 120 couples with the plunger plug 245 and is shown in FIGS. 3A, 3B, and 3C as exploded for assembly purposes. FIG. 2 illustrates the plunger tip 283 fully inserted into the plunger plug 245 and FIG. 9 illustrates a cross section of the plunger tip 283 inserted into the plunger plug 245. The plunger tip 283 may be removably coupled with a plug opening 284 (FIG. 3C) of the plunger plug 245. Referring to FIGS. 3A, 3B, and 3C, in one embodiment, the plunger tip 283 may include one or more barbs 288 and an alignment peg 289. The plunger tip 283 couples with the plunger plug 245 such that they move as one piece within the multistage syringe 100. In one embodiment, the alignment peg 289 may couple with an alignment o-ring 257. It is contemplated that plunger seals 255 (FIG. 2) on the plunger plug 245 may, over time, wear out resulting in reduced interference fit (i.e., seal) between the plunger plug 245 and the first inner wall 435 (FIG. 4A) of the first barrel channel 400 (FIG. 4A). In this embodiment, the alignment o-ring 257 may provide an outward biasing force on the plunger plug 245 when the plunger tip 283 is coupled to the plug opening 284 as shown in FIG. 9. The outward biasing force will maintain the seal between the plunger plug 245 and the first inner wall 435 and the plunger plug 245 and the shuttle aperture 315 (FIG. 3A) over a greater duration of time than an embodiment without the alignment o-ring 257.

In one embodiment, the plunger tip 283 may be coupled to the plunger plug 245 through an interference fit. In one embodiment, an adhesive may also be used to secure the plunger tip 283 and the plunger plug 245. It is contemplated that, in one embodiment, a simple o-ring (e.g., alignment o-ring 257 modified to create an interference fit and slidably couple with the first inner wall 435 of FIG. 4A) could be coupled to the plunger tip 283 in lieu of the plunger plug 245. In one embodiment, Polytetrafluoroethylene (PTFE, a.k.a., Teflon) may be used for the plunger plug 245 or for the combination of the simple o-ring and plunger tip 283. PTFE may reduce the risk of contamination of the fluid in the multistage syringe due to its chemical resistance and inert nature.

The plunger handle 275, at the proximal end 241 of the plunger assembly 120, may be of any diameter to allow a user to firmly grasp the plunger assembly 120. The plunger handle 275 may couple with the neck portion 270 to define the plunger 250 as shown in FIGS. 2, 3A, 3B, and 3C. The plunger handle 275 may be coupled to the neck portion 270 by, but not limited to, an adhesive, threaded coupling, an interference fit or the like. In one embodiment, the plunger handle 275 and the neck portion 270 may be a single piece of material. It is contemplated that, in this embodiment, the plunger handle 275 comprises an equipment coupler 242 at proximal end 241 (FIG. 2) and configured to secure an external piece of equipment (not shown) to the plunger assembly 120 to actuate the multistage syringe 100. The equipment coupler 242 may be a threaded aperture, a threaded protrusion, a bayonet coupler, retaining ring coupler, post and pin coupler, and the like. The piece of equipment may be a linear actuator, a lever actuator, pneumatic actuator, stepper motor driven actuator, rotated cam driven actuator, and the like. It is contemplated that the piece of equipment may accurately and automatically control the amount of fluid that is dispersed and/or aspirated by the multistage syringe 100.

The plunger assembly 120 slidably couples along or parallel with the central axis 200 and creates an interference fit with the first barrel channel 400 (FIG. 4A) and cooperates with the second barrel seal assembly 265 to create an interference fit with a second barrel channel 530 (FIG. 5A). The plunger plug 245 may include one or more plunger seals 255 and the plug opening 284. The plunger seals 255 are sized to create an interference fit and slidably couple with the first inner wall 435 (FIGS. 4A and 4B) of the first barrel channel 400 defined by the inner first barrel radius 430. The first barrel channel 400 is described hereinafter in relation to FIGS. 4A and 4B. The plunger seals 255 of the plunger plug 245 may provide a seal between the plunger assembly 120 and the walls of the first barrel channel 400. As used throughout, the term "seal" indicates a barrier created by two objects which separates two volumes so as to prevent anything from passing between the two volumes. For examples, and not by way of limitation, a seal may be created by an interference fit between two objects such as the plunger 250 and the first inner wall 435 (FIG. 4A). The two volumes may be a first volume, "before" the plunger 250, towards the distal end 342 of the multistage syringe 100 and a second volume, "after" the plunger 250, towards the proximal end 241 of the multistage syringe 100.

Still referring to FIGS. 2, 3A, 3B, and 3C, a second barrel seal assembly 265 may cooperate with the plunger assembly 120 and be configured to provide a seal between the plunger assembly 120 and the second barrel channel 530 (FIG. 5A) of the second barrel 115 when the plunger 250 is retracted toward a proximal end 241 of the multistage syringe 100. In other words, the plunger 250 and the second barrel seal assembly 265 cooperate to maintain a seal as the plunger 250 transitions between a distal end 342 of the multistage syringe 100 and a proximal end 241 of the multistage syringe 100. The second barrel seal assembly 265 may include a shuttle 330 and a first gasket 320. The shuttle 330 may have an outer shuttle diameter 335 (FIG. 3B) that is about equal to two times (2×) the inner second barrel radius 515 (FIG. 5B). The shuttle 330 may slidably couple with a second inner wall 540 (FIG. 5A) of the second barrel channel 530 (FIGS. 5A and 5B). The first gasket 320 may form a seal between the shuttle 330 and the second inner wall 540 of the second barrel 115. Another seal may be created between the first gasket aperture 310 (FIGS. 3A and 3C) of the first gasket 320 and the taper seal 280 of the neck portion 270 when the plunger plug 245 couples with the shuttle 330 (i.e., the plunger plug 245 is retracted into the shuttle 330). FIG. 9 illustrates the relationship between the first gasket 320 and the taper seal 280 and the plunger plug 245 and the shuttle 330. The shuttle 330 may include the shuttle aperture 315, retainer lip 316 (FIGS. 2 and 3A) disposed through a shuttle body 350 and centered along the central axis 200. The shuttle 330 may also include a gasket retainer 340 (FIGS. 3B and 3C) and a retainer lip 316 (FIG. 11). The gasket retainer 340 retains the first gasket 320 in relation to the shuttle 330. The gasket retainer 340 may be a set of clips or a ring centered on the central axis 200. The retainer lip 316 constricts the shuttle aperture 315 to about a diameter that about matches the necked diameter 285. The shuttle engagement ring 295 of the plunger 250 couples with the retainer lip 316 of the shuttle 330.

Referring to FIGS. 2, 3A, 3B, and 3C, the multistage syringe 100 includes a spring assembly 360 that may include a first spring retainer 365, a second spring retainer 370, and a spring 375. The spring 375 is captured or retained between the first spring retainer 365, the second spring retainer 370, and the second barrel channel 530 (FIG. 5A). The spring assembly 360 exerts a biasing force which returns the shuttle 330 to a rest position near the second barrel lip 535 when the plunger assembly 120 is not in a retracted position. The biasing force may also serve to form a seal between the shuttle 330 and the first barrel lip 420 (FIG. 4A) of the first barrel 110. The function of the spring assembly 360 is described in greater detail below. It is contemplated that the spring assembly 360 is not necessary for operation of the multistage syringe 100 and may not be included in all embodiments. The spring assembly 360 enables repeatable dispensing of fluid from the second barrel 115 by maintaining the coupling of the plunger plug 245 and the shuttle 330. It is contemplated that the spring assembly 360 may not be needed if differing materials are used for the plunger plug 245 and shuttle 330 or the use of a snap o-ring on the plunger plug 245 and a retaining ring within the shuttle body 350 are used.

In one embodiment, the multistage syringe 100 may comprise a dispensing tip 105. At a distal end 342, the dispensing tip 105 comprises a tip end 210 and a delivery channel 205. The delivery channel 205 may be axially aligned along a central axis 200 of the multistage syringe 100 and fluidly coupled to a first barrel channel 400 (FIG. 4A) of the first barrel 110. In one embodiment, the delivery channel 205 may be offset from the central axis 200. In one embodiment, the dispensing tip 105 may be removably coupled to the multistage syringe 100 to allow for different dispensing apparatuses to couple with the multistage syringe 100 for different applications. Examples of dispensing apparatuses include, but are not limited to, a rigid tube, a flexible tube, blunt end needle, beveled end needle, or combinations thereof. In one embodiment, the dispensing tip 105 may be configured to secure a needle, a flexible tube, a spray nozzle, or the like without the need for the tip end 210. It is contemplated that the multistage syringe 100 can be used without the dispensing tip 105.

In one embodiment, the tip end 210 may include a tapered gasket 211 which may provide an interface between the multistage syringe 100 and medical devices, medical tools, an aperture, or the like in which the fluid is either dispensed from the multistage syringe 100 or drawn into the multistage syringe 100. For example, but not limited to, the tapered gasket 211 may couple with an aperture (not shown) of a medical device (not shown) or dispensing apparatuses and create a seal with the aperture. In one embodiment, a flex joint 215 may allow the tapered gasket 211 to not be axially aligned with the central axis 200 and still allow for the seal with the aperture and a flow of fluid through the dispensing tip 105. In one embodiment, the flex joint 215 may be to retain an o-ring on the dispensing tip 105. For example, and not by way of limitation, the o-ring seals the dispensing tip 105 with a pipette tip and the like.

The dispensing tip 105 may comprise a barbed end 220 with one or more barbs. In one embodiment, the barbed end 220 includes a first barb 225 and a second barb 230. The first barb 225 and the second barb 230 provide an interference fit with a first barrel channel 400 (FIG. 4A). In one embodiment, the interference fit may include an adhesive to further secure the dispensing tip 105 to the first barrel 110 and increase the integrity of the seal between the dispensing tip 105 to the first barrel 110. The first barb 225 and the second barb 230 seal the dispensing tip 105 and the first barrel 110 to ensure the contents of the first barrel channel 400 do not escape between the dispensing tip 105 and the first barrel 110. Alternative example of the first barb 225 and the second barb 230 may be, and not by way of limitations, an interference fit, adhesive, threaded coupling, or an o-ring.

Figure 6:
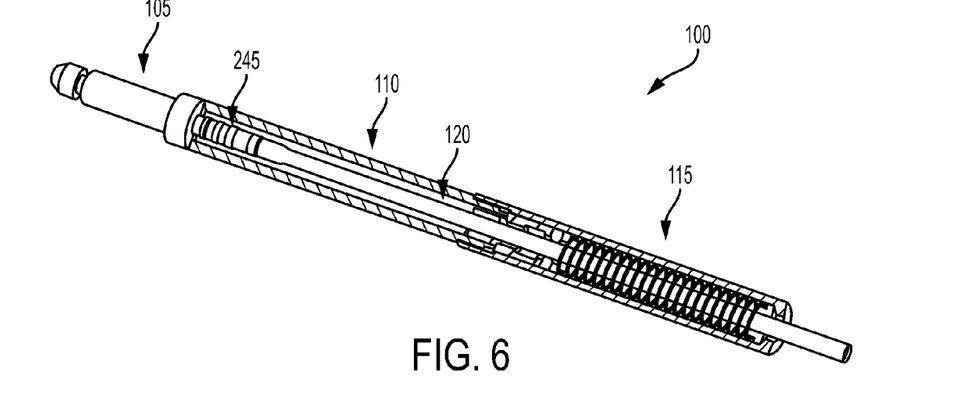
FIG. 6 is a perspective view of the multistage syringe in a dispensed position according to one or more embodiments shown and described herein.

Referring to FIG. 6, the multistage syringe 100 is shown in a dispensed position with the plunger plug 245 near the dispensing tip 105 at the distal end of the multistage syringe 100. The first barrel 110 and the second barrel 115 of multistage syringe 100 are substantially empty in the dispensed position. However, there may be fluid in the dispensing tip 105. In the dispensed position, the plunger assembly 120 is fully inserted into the multistage syringe 100. In one example, and not limited to, the plunger assembly 120 is fully inserted into the multistage syringe 100 such that the plunger plug is in proximity to the distal end 342 (FIG. 2).

Figure 7:
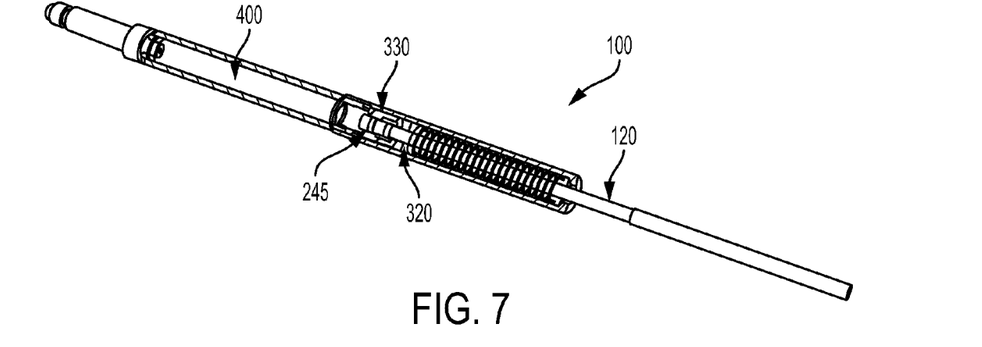
FIG. 7 is another view of the multistage syringe in a transition position according to one or more embodiments shown and described herein.

Referring to FIG. 7, the multistage syringe 100 is shown in a transition position with the plunger plug 245 coupled to the shuttle 330. In this position, the fluid may fill a portion of the first barrel channel 400.

Figure 8:
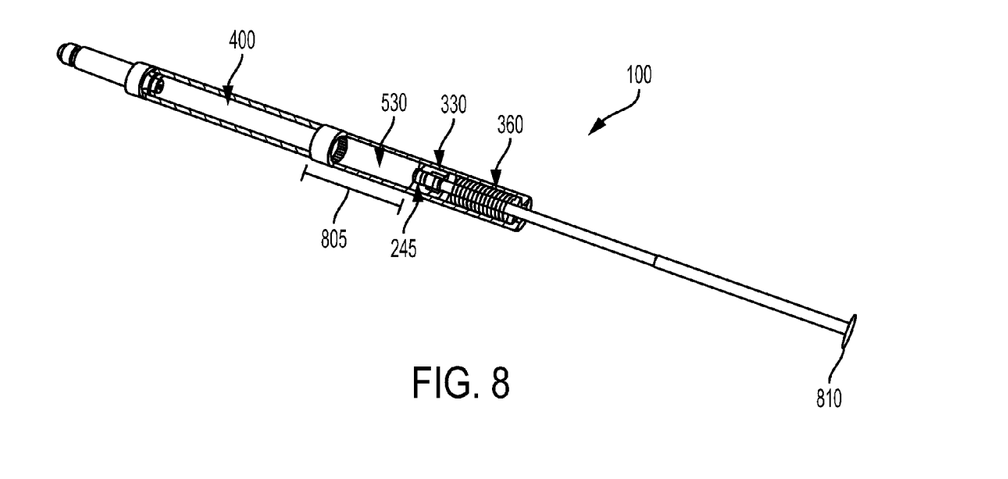
FIG. 8 is yet another view of the multistage syringe in a aspirated position according to one or more embodiments shown and described herein.

Referring to FIG. 8, in an aspirated position, the plunger plug 245 may be coupled to the shuttle 330 in proximity to the proximal end of the multistage syringe 100. In this position, the fluid may fill occupy a portion of both the first barrel channel 400 and the second barrel channel 530. In the aspirated position, the plunger assembly 120 is in a retracted position. The spring assembly 360 may be configured to provide a bias force that is large enough in magnitude to transition the shuttle 330 to the rest position unassisted but small enough in magnitude to not impede the transition of the plunger assembly 120 to the fully retracted position or cause a malfunction of the multistage syringe 100. In some embodiments, the plunger assembly 120 may include a large head 810 to allow for easier actuation of the plunger assembly 120.

Referring to FIGS. 6, 7, and 8, the actuation of the plunger assembly 120 transitions the multistage syringe 100 from the dispensed position (i.e., FIG. 6) to the transition position (i.e., FIG. 7) and from the transition position to the aspirated position (i.e., FIG. 8). The transition of the plunger 250 from the dispensed position to the transition position fills a portion of the first barrel channel 400 "before" the plunger 250 with the fluid. The transition of the plunger 250 from the transition position to the aspirated position fills a portion of the second barrel channel 530 "before" the plunger 250 with fluid.

The multistage syringe 100 operates like a simple pump where an airtight seal in a barrel is transitioned between respective endpoints of the barrel to either dispense or aspirate fluid out of an orifice at one end of the barrel. The multistage syringe 100 has the added complexity of multiple barrels, each with a differing internal diameter. A barrel seal assembly (e.g., second barrel seal assembly 265) maintains the seal during the transition of the plunger 250 through the respective barrel. Referring specifically to the two barrel embodiment illustrated in FIGS. 6, 7, and 8, the airtight seal is maintained between the plunger assembly 120 (FIG. 2) and the first barrel channel 400 (FIG. 4A) and the second barrel channel 530 (FIG. 5A) during the transition of the plunger 250 between the dispense position and the aspirate position. It is contemplated, for example during aspiration of the multistage syringe 100, that the transition position begins when the taper seal 280 contacts the shuttle 330 and ends when the shuttle 330 (i.e., second barrel seal assembly 265) is no longer in contact with the first barrel lip 420. The opposite is true for dispensing of a fluid from the multistage syringe 100.

Pressure on both sides of the plunger 250 is equalized to maintain the seal as the plunger 250 is transitioned within multistage syringe 100. The area "after" the plunger 250, towards the proximal end 241 of the multistage syringe 100, is fluidly coupled to the atmosphere where the plunger handle 275 exits the second barrel 115. When the plunger 250 is positioned in the first barrel 110, the shuttle aperture 315 (FIG. 3A) in the shuttle body 350 (FIG. 3A) fluidly couples the second barrel 115 to the area "after" the plunger 250. In other words, the necked diameter 285 (FIG. 2) is smaller than the shuttle aperture 315 and the first gasket aperture 310 (FIG. 3A), allowing the fluid coupling between the two barrels. When the multistage syringe 100 is in the transition position, the taper seal 280 contacts the shuttle body 350 and blocks the fluid coupling between the two barrels. In other words, the contact between the taper seal 280 and the shuttle body 350 cooperate to create a seal between the plunger assembly 120 and the second barrel seal assembly 265 when needed to maintain the seal within the multistage syringe 100 between the plunger assembly 120 and the individual barrels. In one embodiment, the seal may be created when the taper seal 280 couples with the first gasket 320. It is contemplated that the tapered diameter 290 (FIG. 2) of the taper seal 280 may be about equal to the necked diameter 285 of the neck portion 270 if the area behind the plunger 250 towards the proximal end 241 is fluidly coupled to the atmosphere.

Referring back to FIGS. 4A and 4B, a first barrel volume of the first barrel channel 400 is about equal to a first barrel length 440 multiplied by the product of the square of the inner first barrel radius 430 and pi (e.g. 3.1416). Referring to FIGS. 5A and 5B, a second barrel volume of the second barrel channel 530 is about equal to a second barrel length 505 multiplied by the product of the square of the inner second barrel radius 515 and pi. In some embodiments, the fluid may only fill a portion of the second barrel volume due the combined space that the spring assembly 360 and shuttle 330 occupy. In this embodiment, the second barrel volume of the second barrel channel 530 is about equal to a second free length 805 multiplied by the product of the square of the inner second barrel radius 515 and pi. The total volume of fluid in the multistage syringe 100 is about equal to the sum of the first barrel volume, the volume of fluid in the dispensing tip 105, and the second barrel volume.

Referring to FIGS. 6, 7, and 8, it should be understood that the volume of the multistage syringe 100 may range from the volume of the multistage syringe in the dispensed position to about the volume of the multistage syringe 100 in the aspirated position. It should also be understood, per linear rate of movement of the plunger assembly 120, the rate (i.e., speed) of dispensing or aspiration of the fluid is different between the first barrel 110 and the second barrel 115 because of the difference in inner diameters and/or the different barrel lengths between the first barrel 110 and the second barrel 115. In one embodiment, the first barrel length 440 and/or the second barrel length 505 may be varied to change the rate of dispensing or aspiration of the multistage syringe 100. In one embodiment, the inner first barrel radius 430 and/or the inner second barrel radius 515 may be varied to change the rate of dispensing or aspiration of the multi-stage syringe 100. In one embodiment, combinations of the first barrel length 440, the second barrel length 505, the inner first barrel radius 430 and/or the inner second barrel radius 515 may be varied to change the rate of dispensing or aspiration of the multistage syringe 100.

Figure 4B:
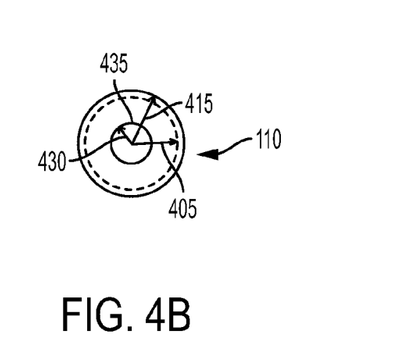
FIG. 4B is a transverse cross-sectional view of the first barrel according to one or more embodiments shown and described herein.
Figure 5A:
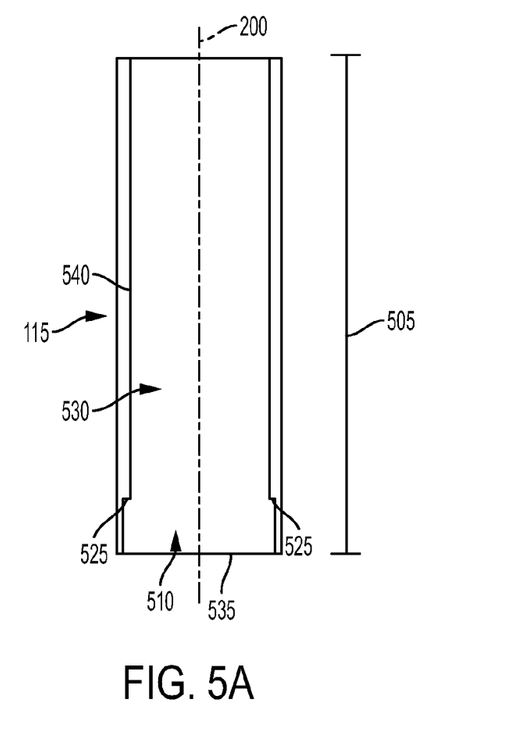
FIG. 5A is a lengthwise cross-sectional view of a second barrel according to one or more embodiments shown and described herein.
Figure 5B:
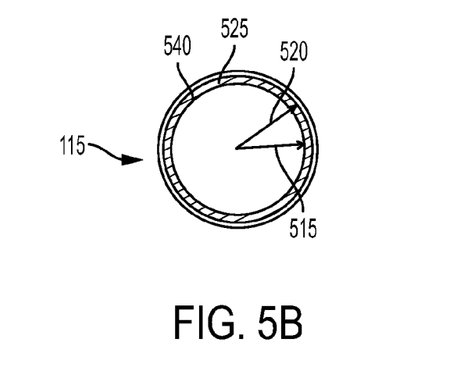
FIG. 5B is a transverse cross-sectional view of the second barrel according to one or more embodiments shown and described herein.

Still referring to FIGS. 6, 7, and 8, in one embodiment, the inner second barrel radius 515 (FIGS. 5A and 5B) may be smaller than the inner first barrel radius 430 (FIGS. 4A and 4B). The first barrel volume may smaller than the second barrel volume allowing for a smaller volume of fluid to be either dispensed or aspirated during the transition between the dispense position and the transition position and a larger volume of fluid to be either dispensed or aspirated during the transition between the transition position and the aspiration position. In other words, when the plunger plug 245 is between the dispensed position and transition position, the multistage syringe may perform as any conventional syringe. A portion of fluid may be drawn up into the first barrel channel 400 via vacuum created between the plunger plug 245 and the first inner wall 435 of the first barrel 110. During this transition to the transition position, there is not a seal between the plunger assembly 120, the shuttle 330, and the first gasket 320. A seal may be required between the plunger plug 245 and the second barrel 115 from the point in actuation time just before the plunger plug 245 releases contact with the first inner wall 435 of the first barrel 110, roughly near the transition position. An increase in diameter (i.e. tapered diameter 290) of the plunger 250 just behind the plunger plug 245 creates a seal with the shuttle aperture 315 (FIG. 3A) of the shuttle 330 at or just before the plunger plug 245 releases contact with the first inner wall 435 of the first barrel 110 (i.e., the transition to the transition position). For the remaining part of the actuation stroke (i.e. transitioning the plunger assembly 120 between positions) until the aspiration position, the seal between the first gasket 320 and the second inner wall 540 (FIG. 5A) and the taper seal 280 (FIG. 3A) and the shuttle aperture 315, creates a vacuum that draws fluid into the multistage syringe 100. It is during the transition from the transition position to the aspirated position of the cycle that more volume is drawn in to the multistage syringe 100 as, in some embodiments, the inner second barrel radius 515 (FIG. 5B) may be larger than that of the inner first barrel radius 430 (FIG. 4B).

FIG. 9 depicts a cross-sectional top view of the shuttle 330 and the plunger assembly 120 of the multistage syringe 100 in the aspirated position. It should be understood, that in the transition position, the seal between the taper seal 280 and the shuttle aperture 315 is complete however, the plunger 250 may not be fully inserted into the shuttle aperture 315. In one embodiment, when the seal is created between the taper seal 280 and the shuttle aperture 315, the interference fit between the two moves the shuttle 330 as the multistage syringe 100 is further transitioned between positions (e.g. the aspirated position). In one embodiment, when the shuttle engagement ring 295 is in contact with the retainer lip 316, the plunger assembly 120 and the shuttle 330 move as the multistage syringe is further transitioned between positions (e.g., aspirated position).

As explained hereinbefore, the spring assembly 360 exerts a biasing force which returns the shuttle 330 to a rest position near the second barrel lip 535 when the plunger assembly 120 is not in a retracted position (i.e., when the plunger plug 245 is not in contact with the shuttle 330) and may also serve to form a seal between the shuttle 330 and the first barrel lip 420. The seal may be created before the plunger plug 245 enters the first barrel 110 when for example, the multistage syringe 100 is transitioned from the transition position to the dispense position.

In exemplary embodiments, the plunger plug 245, the barrel gasket 240, and the first gasket 320 may be made from a compressible material that may allow for deformation of the plunger plug 245, the barrel gasket 240, and the first gasket 320 and still allow for a seal between parts. For example, the compressible material may include, but not limited to, rubber, rubber derivatives, PTFE, malleable plastics, and the like. The dispensing tip 105, first barrel 110, second barrel 115, and parts of the plunger 250 may be made of or comprise any rigid material such as plastic, polymer (PEEK, polyacetals, PK, for example), rubber, ceramics, or metal or combinations thereof.

Referring to FIG. 2, the length and/or the radius of the first barrel 110 and/or the second barrel 115 may be varied to change the amount of fluid dispensed or aspirated by the multistage syringe 100. The combination of the second barrel seal assembly 265 and the plunger assembly 120 sequences the transition of seals between the first barrel 110 and the second barrel 115 to dispense or aspirate fluid with the multistage syringe 100. The shuttle 330 and the first barrel lip 420 (FIG. 4A) may provide a seal when the plunger plug 245 is positioned in the first barrel 110. The first gasket 320 and the second inner wall 540 (FIG. 5A) of the second barrel 115 may provide a seal when the plunger plug 245 is positioned in the second barrel 115. In the transition position, the shuttle 330 and the first barrel lip 420 and the first gasket 320 and the second inner wall 540 seal the first barrel 110. In other words, the first barrel 110 volume is always segregated from the second barrel 115 volume until the multistage syringe 100 is in the aspirate position, i.e., the second barrel seal assembly 265 is not in contact with the first barrel lip 420.

Figure 10:
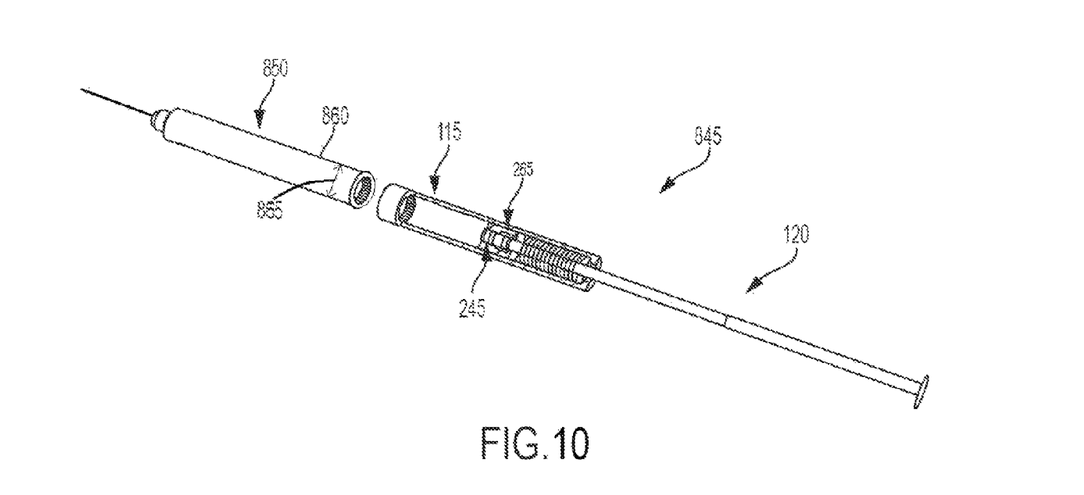
FIG. 10 is an isometric view of a syringe kit according to one or more embodiments shown and described herein.

Referring now to FIG. 10, in one embodiment, a syringe kit 845 comprises the second barrel 115, the second barrel seal assembly 265, and the plunger assembly 120. The syringe kit 845 may be used to modify an existing syringe 850. The second barrel 115 couples to a syringe barrel 860 of the existing syringe 850 such that a syringe barrel channel of the syringe barrel 860 aligns with the second barrel channel 530 (FIG. 5A) of the second barrel 115 along a central axis 200 (FIG. 2). The inner receiver radius 520 (FIG. 5B) may be sized to accommodate an outer syringe diameter 865 such that the existing syringe 850 slidably couples with the second barrel 115. The existing syringe 850 may be coupled to the second barrel 115 as described hereinbefore in relation to the first barrel 110 and the second barrel 115. In one embodiment, the collar space 235 may be present. The plunger plug 245 is sized to provide an airtight seal between the plunger assembly 120 and the syringe barrel channel. The seal between the plunger assembly 120 and the syringe barrel channel and the second barrel channel 530 is maintained as the plunger 250 transitions between the syringe barrel channel and the second barrel channel 530 such as that described hereinbefore. In other words, the plunger 250 and the second barrel seal assembly 265 cooperate to maintain a seal as the plunger tip transitions between a distal end and a proximal end of the combination of the syringe and the syringe kit.

It should be understood that the present disclosure is not limited to a multistage syringe 100 with only a single first barrel 110, second barrel 115, plunger assembly 120, and second barrel seal assembly 265. The present disclosure is scalable to meet specific needs. For example, and not by limitation, multiple second barrels and associated second barrel seal assemblies may be stacked along the central axis 200 to increase the total volume of the multistage syringe 100. In this example, as described hereinbefore, the plunger plug 245 will couple with the shuttle 330 when transitioning through the second barrel 115. The shuttle 330 may than couple with another shuttle (e.g., a third shuttle) when the plunger plug is transitioning through a third barrel coupled to the second barrel 115, and so on. The successive shuttles will telescope into each other as the plunger plug 245 is transitioned towards the proximal end 241. The opposite is true as the plunger plug 245 is transitioned towards the distal end 342. In one embodiment, the multiple barrels (e.g., first barrel 110 and second barrel 115 only or first barrel 110 and successive second barrels 115) may comprise an internally stepped piece of glass, plastic, ceramic, or the like. In other words, it is contemplated that the multiple barrels are a single piece of material.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A multistage syringe comprising a first barrel, a second barrel, a second barrel seal assembly, and a plunger assembly wherein:
    the first barrel comprises a first barrel channel;
    the second barrel comprises a second barrel channel;
    the first barrel couples to the second barrel such that the first barrel channel aligns with the second barrel channel along a central axis;
    the plunger assembly comprises a plunger coupled to a plunger handle;
    the plunger slidably couples with the first barrel channel along the central axis;
    the second barrel seal assembly slidably couples with the second barrel channel along the central axis; and
    the plunger and the second barrel seal assembly cooperate to maintain a seal as the plunger transitions between a distal end of the multistage syringe and a proximal end of the multistage syringe.

2. The multistage syringe as claimed in claim 1 further comprises a dispensing tip comprising a delivery channel and a tip end, wherein the dispensing tip is coupled to the first barrel and is axially aligned with the first barrel channel.

3. The multistage syringe as claimed in claim 2 wherein the tip end comprises a tapered gasket and a flex joint.

4. The multistage syringe as claimed in claim 1 wherein:
    the first barrel channel comprises a first inner barrel volume;
    the second barrel channel comprises a second inner barrel volume; and
    the second inner barrel volume is greater than the first inner barrel volume.

5. The multistage syringe as claimed in claim 1 wherein:
    the first barrel channel comprises a first inner barrel volume;
    the second barrel channel comprises a second inner barrel volume; and
    the first inner barrel volume is greater than the second inner barrel volume.

6. The multistage syringe as claimed in claim 1 wherein:
    the first barrel channel comprises a first inner barrel volume;
    the second barrel channel comprises a second inner barrel volume; and
    the first inner barrel volume is about equal to the second inner barrel volume.

7. The multistage syringe as claimed in claim 1 wherein the plunger handle comprises an equipment coupler configured to secure an external piece of equipment the plunger assembly to actuate the multistage syringe.

8. The multistage syringe as claimed in claim 1 wherein:
    the plunger assembly comprises a plunger plug;
    the plunger comprises a plunger tip;
    the plunger tip removably couples to the plunger plug;
    the plunger plug is at a distal end of the plunger assembly; and
    the plunger handle is at a proximal end of the plunger assembly.

9. The multistage syringe as claimed in claim 8 wherein:
    the plunger plug comprises a plug opening and one or more plunger seals;
    the plunger tip removably couples to the plug opening of the plunger plug; and
    the one or more plunger seals slidably couple with the first barrel channel.

10. The multistage syringe as claimed in claim 9 wherein:
    the second barrel seal assembly comprises a shuttle and a first gasket; and
    the first gasket maintains a seal between the shuttle and the second barrel channel when the plunger plug couples with the shuttle.

11. The multistage syringe as claimed in claim 10 wherein:
    the plunger assembly comprises a taper seal and a shuttle engagement ring;
    the taper seal maintains a seal between the plunger assembly and the shuttle when the plunger plug couples with the shuttle; and
    the shuttle engagement ring couples with the shuttle when the plunger plug transitions into the second barrel channel.

12. The multistage syringe as claimed in claim 1 wherein the plunger tip comprises an o-ring; and
    the o-ring slidably couples with the first barrel channel.

13. A syringe kit comprising a second barrel, a second barrel seal assembly, and a plunger assembly wherein:
    the second barrel comprises a second barrel channel;
    the second barrel seal assembly slidably couples with the second barrel channel along a central axis;
    the plunger assembly comprises a plunger coupled to a plunger handle;
    the second barrel is configured couple with a syringe comprising a syringe barrel and a syringe barrel channel such that the syringe barrel channel aligns with the second barrel channel along the central axis;
    the plunger slidably couples with the syringe barrel channel along the central axis; and
    the plunger and the second barrel seal assembly cooperate to maintain a seal as the plunger transitions between a distal end and a proximal end of the combination of the syringe and the syringe kit.

14. The syringe kit as claimed in claim 13 wherein:
    the syringe barrel channel comprises a syringe inner barrel volume;
    the second barrel channel comprises a second inner barrel volume; and
    the second inner barrel volume is greater than the syringe inner barrel volume.

15. The syringe kit as claimed in claim 13 wherein:
    the syringe barrel channel comprises a syringe inner barrel volume;
    the second barrel channel comprises a second inner barrel volume; and
    the syringe inner barrel volume is greater than the second inner barrel volume.

16. The syringe kit as claimed in claim 13 wherein:
the syringe barrel channel comprises a syringe inner barrel volume;
the second barrel channel comprises a second inner barrel volume; and
the syringe inner barrel volume is about equal to the second inner barrel volume.

17. The syringe kit as claimed in claim 13 wherein:
the plunger assembly comprises a plunger plug;
the plunger comprises a plunger tip;
the plunger tip removably couples to the plunger plug;
the plunger plug is at a distal end of the plunger assembly; and
the plunger handle is at a proximal end of the plunger assembly.

18. The syringe kit as claimed in claim 17 wherein:
the plunger plug comprises a plug opening and one or more plunger seals;
the plunger tip removably couples to the plug opening of the plunger plug; and
the one or more plunger seals slidably couple with the syringe barrel channel.

19. The syringe kit as claimed in claim 18 wherein:
the second barrel seal assembly comprises a shuttle and a first gasket; and
the first gasket maintains a seal between the shuttle and the second barrel channel when the plunger plug couples with the shuttle.

20. The syringe kit as claimed in claim 19 wherein:
the plunger assembly comprises a taper seal and a shuttle engagement ring;
the taper seal maintains a seal between the plunger assembly and the shuttle when the plunger plug couples with the shuttle; and
the shuttle engagement ring couples with the shuttle when the plunger plug transitions into the second barrel channel.

* * * * *

UNITED STATES PATENT AND TRADEMARK OFFICE
CERTIFICATE OF CORRECTION

PATENT NO. : 9,579,687 B2
APPLICATION NO. : 14/752112
DATED : February 28, 2017
INVENTOR(S) : Paul J. Wright It is certified that error appears in the above-identified patent and that said Letters Patent is hereby corrected as shown below:

In the Specification

Column 1, Line 50:
"The second barrel is configured couple with a syringe"
Should read:
--The second barrel is configured coupled with a syringe--;

Column 2, Line 66:
"delivers different volumes of fluid at near identical liner"
Should read:
--delivers different volumes of fluid at near identical linear--;

Column 7, Line 16:
"position, the fluid may fill occupy a portion of both the first"
Should read:
--position, the fluid may fill or occupy a portion of both the first--;

Column 8, Line 28:
"fluid may only fill a portion of the second barrel volume due"
Should read:
--fluid may only fill a portion of the second barrel volume due to--;

Column 8, Line 61:
"4B). The first barrel volume may smaller than the second"
Should read:
--4B). The first barrel volume may be smaller than the second--;

Signed and Sealed this
Second Day of January, 2018

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,579,687 B2

Column 9, Line 59:
"example, the compressible material may include, but not"
Should read:
--example, the compressible material may include, but not be--;

Column 10, Line 55:
"through the second barrel 115. The shuttle 330 may than"
Should read:
--through the second barrel 115. The shuttle 330 may then--; and In the Claims Column 12, Claim 13, Line 44:
"the second barrel is configured couple with a syringe"
Should read:
--the second barrel is configured to be coupled with a syringe--.